(12) United States Patent
Lu et al.

(10) Patent No.: US 7,321,011 B2
(45) Date of Patent: Jan. 22, 2008

(54) SELF-EMULSIFYING COPOLYMER

(75) Inventors: Shao Xiang Lu, Plainsboro, NJ (US); Mohamed Kanji, Edison, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/622,689

(22) Filed: Jul. 21, 2003

(65) Prior Publication Data

US 2005/0020769 A1    Jan. 27, 2005

(51) Int. Cl.
C08L 83/12 (2006.01)

(52) U.S. Cl. ............ 524/588; 528/31; 528/38; 528/26; 528/28; 528/41; 525/479; 556/444

(58) Field of Classification Search ............. 524/588; 556/444; 528/28, 26, 31, 38, 41; 525/479
See application file for complete search history.

(56) References Cited

U.S. PATENT DOCUMENTS

| | | |
|---|---|---|
| 2,823,195 A | 2/1958 | Shorr et al. |
| 2,823,218 A | 2/1958 | Speier et al. |
| 3,723,566 A | 3/1973 | Thompson et al. |
| 4,322,400 A | 3/1982 | Yuhas |
| 4,822,852 A * | 4/1989 | Wittmann et al. ............ 525/66 |
| 5,262,505 A | 11/1993 | Nakashima et al. |
| 5,407,986 A | 4/1995 | Furukawa et al. |
| 5,412,004 A | 5/1995 | Tachibana et al. |
| 5,473,041 A | 12/1995 | Itoh |
| 5,567,428 A | 10/1996 | Hughes |
| 5,725,882 A | 3/1998 | Kuman et al. |
| 5,837,223 A | 11/1998 | Barone et al. |
| 5,874,069 A | 2/1999 | Mendolia et al. |
| 5,919,441 A | 7/1999 | Mendolia et al. |
| 5,969,172 A | 10/1999 | Nye |
| 5,981,680 A | 11/1999 | Petroff et al. |
| 5,985,297 A | 11/1999 | Mellul et al. |
| 6,045,782 A | 4/2000 | Krog et al. |
| 6,051,216 A | 4/2000 | Barr et al. |
| 6,060,072 A | 5/2000 | Konik et al. |
| 6,103,250 A | 8/2000 | Brieva et al. |
| 6,177,091 B1 | 1/2001 | Bara et al. |
| 6,353,076 B1 | 3/2002 | Barr et al. |
| 6,362,287 B1 | 3/2002 | Chorvath et al. |
| 6,362,288 B1 | 3/2002 | Brewer et al. |
| 6,376,078 B1 | 4/2002 | Inokuchi |
| 6,423,324 B1 | 7/2002 | Murphy et al. |
| 6,426,062 B1 | 7/2002 | Chopra et al. |
| 6,451,295 B1 | 9/2002 | Cai et al. |
| 6,503,632 B1 | 1/2003 | Hayashi et al. |
| 6,524,598 B2 | 2/2003 | Sunkel et al. |
| 6,541,017 B1 | 4/2003 | Lemann et al. |
| 6,569,955 B1 | 5/2003 | Brewer et al. |
| 6,916,464 B2 | 7/2005 | Hansenne et al. |
| 2002/0028223 A1 | 3/2002 | Vatter et al. |
| 2002/0048557 A1 | 4/2002 | Cai et al. |
| 2002/0051758 A1 | 5/2002 | Cai et al. |
| 2003/0068348 A1 | 4/2003 | Ferrari et al. |
| 2003/0072730 A1 | 4/2003 | Tournilhac |
| 2003/0082129 A1 | 5/2003 | Buckingham et al. |
| 2003/0170188 A1 | 9/2003 | Ferrari et al. |
| 2003/0228333 A1 | 12/2003 | Fecht et al. |
| 2003/0232030 A1 | 12/2003 | Lu et al. |
| 2003/0235548 A1 | 12/2003 | Lu |
| 2003/0235552 A1 | 12/2003 | Yu |
| 2003/0235553 A1 | 12/2003 | Lu et al. |
| 2004/0001799 A1 * | 1/2004 | Lu et al. ............. 424/70.122 |
| 2004/0115153 A1 | 6/2004 | Yu |
| 2004/0115154 A1 | 6/2004 | Yu |
| 2004/0120912 A1 | 6/2004 | Yu |
| 2004/0126336 A1 | 7/2004 | Hansenne et al. |
| 2004/0170586 A1 | 9/2004 | Ferrari et al. |
| 2004/0180032 A1 | 9/2004 | Manelski et al. |
| 2004/0197285 A1 | 10/2004 | Van Dort |
| 2004/0223936 A1 | 11/2004 | Fecht et al. |
| 2005/0009989 A1 | 1/2005 | Liew et al. |
| 2005/0020769 A1 | 1/2005 | Lu et al. |
| 2005/0089492 A1 | 4/2005 | Lu et al. |
| 2005/0158260 A1 | 7/2005 | Ferrari et al. |
| 2006/0193801 A1 | 8/2006 | Blin et al. |

FOREIGN PATENT DOCUMENTS

| | | |
|---|---|---|
| EP | 0 377 447 A2 | 7/1990 |
| EP | 0 594 285 A2 | 4/1994 |
| EP | 0 693 517 A1 | 1/1996 |
| EP | 0 923 928 | 6/1999 |
| EP | 1 048 686 | 11/2000 |
| EP | 1 068 856 | 1/2001 |

(Continued)

OTHER PUBLICATIONS

Dow Corning® 2-8178 Gellant, Ref. No. 27-1055-01; 35pp., Aug. 2002.
English Language Derwent Abstract of EP 0 923 928, Jun. 23, 1999.
English Language Derwent Abstract of EP 1 068 856, Jan. 17, 2001.
English Language Derwent Abstract of FR 2 765 800, Jan. 15, 1999.
U.S. Appl. No. 11/342,748, filed Jan. 31, 2006, Blin et al.
Dow Corning® 2-8178 Gellant, Ref. No. 27-1055-01, Aug. 2002, 35 pp.
Dow Corning® 2-8178 Gellant, Product Information Personal Care, 6 pp, 2002.
Shin-Etsu Silicones for Personal Care; Product Brochure, KSP-100•101•102•103•104•105 "Hybrid Silicone Powders for Personal Care", Nov. 2000.
Shin-Etsu Silicones for Personal Care; Product Brochure, KSP-200•300 "Hybrid Silicone Powders containing Fluoroalkyl or Phenyl group for Personal Care", Feb. 2001.

*Primary Examiner*—Kuo-Liang Peng
(74) *Attorney, Agent, or Firm*—Oblon, Spivak, McClelland, Maier & Neustadt, P.C.

(57) ABSTRACT

The invention relates to self-emulsifying copolymers, and to compositions, preferably care and/or treatment and/or make-up compositions for keratin and keratinous materials (including the skin, hair, nails, scalp, and/lips of human beings, keratinous fibers, etc.), containing one or more such self-emulsifying copolymers. Methods of making and using the self-emulsifying copolymers and compositions containing them also make up a part of the invention.

18 Claims, No Drawings

FOREIGN PATENT DOCUMENTS

| | | |
|---|---|---|
| EP | 1 266 647 | 12/2002 |
| EP | 1 266 648 | 12/2002 |
| FR | 2 765 800 | 1/1999 |
| GB | 134 8783 | 3/1974 |
| WO | WO 97/36572 | 10/1997 |
| WO | WO 97/36573 | 10/1997 |
| WO | WO 99/47111 | 1/1999 |
| WO | WO 99/06473 | 2/1999 |
| WO | WO 01/09239 A1 | 2/2001 |
| WO | WO 01/97758 A2 | 12/2001 |
| WO | WO 02/17870 A2 | 3/2002 |
| WO | WO 02/17871 A2 | 3/2002 |
| WO | WO 02/089760 A1 | 11/2002 |
| WO | WO 03/013447 A2 | 2/2003 |
| WO | WO 03/105788 A2 | 6/2003 |
| WO | WO 2004/054523 | 7/2004 |
| WO | WO 2004/054524 | 7/2004 |
| WO | WO 2006/060295 | 6/2006 |

* cited by examiner

SELF-EMULSIFYING COPOLYMER

FIELD OF THE INVENTION

The present invention relates to self-emulsifying copolymers, and to compositions, preferably care and/or treatment and/or make-up compositions for keratin and keratinous materials (including the skin, hair, nails, scalp, and/or lips of human beings, keratinous fibers, etc.), comprising one or more such self-emulsifying copolymers. Methods of making and using the self-emulsifying copolymers and compositions containing them also make up a part of the invention.

DETAILED DESCRIPTION OF THE INVENTION

Discussion of the Background

The use of copolymers in cosmetics is known for several purposes. For example, Dow Corning's silicone polyamide copolymers 2-8178 (INCI Name: Nylon-611/Dimethicone Copolymer and PPG-3 Myristyl Ether) and 8179 (INCI Name: Nylon-611/Dimethicone Copolymer) have been used by the present inventors, for example to structure oil phases. The molecular weight of these copolymers may vary from, e.g., about 60,000-150,000, 65,000-140,000, etc., Daltons. Preferred materials have molecular weights in the lower end of these ranges, for example 60,000-70,000, including 62,000, 68,000, etc. Dow Product Information regarding these copolymers is incorporated herein by reference. The structure of these copolymers is as follows:

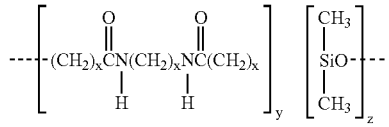

where x, y, and z are appropriate to meet the molecular weight.

In certain situations it would be advantageous for a cosmetically useful copolymer to be self-emulsifiable. Such a property would broaden the use of the material, for example in emulsions, and enhance the ability of the material to form films, form gels, etc.

It is with this goal of self-emulsifiability in mind that the present invention has been made, where new self-emulsifiable copolymers useful in cosmetic and dermatologic areas, as well as other areas, are now provided.

Self-Emulsifying Copolymers

Preferred self-emulsifying copolymers of the invention have a preferred weight average molecular weight of from about 500 to about 500,000 and more, and comprise a chemical structure A as follows:

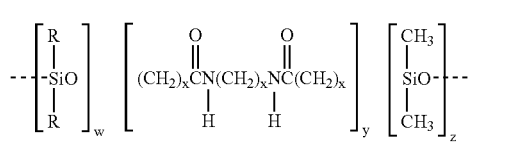

where at least one R is, as discussed below, an oxyalkylene group such as —OEt-, etc., the remaining R, if present, is H or a C1-C12 alkyl group, preferably methyl or ethyl, x, which may be the same or different, is any integer and preferably 1-40 and w, y, and z are appropriate to meet the molecular weight. Preferably z is 0-1000, more preferably 1-1000, even more preferably 1-200, even more highly preferably 1-100 including 10, 20, 30, 40, etc. Preferably w and y are, independently, 1-1000, more preferably 1-200, even more preferably 1-100 including 10, 20, 30, 40, etc., and the ratio y/(w+z) optionally varies from 0.01 to 100, more preferably 1-10, including all values between all ranges. Preferably the ratio z/w varies from 0-1000, including 0-100, 0-10, 2-8, etc, where a value of 0 indicates that z=0, and w is nonzero. Preferably, w is never zero.

Another preferred self-emulsifying copolymer according to the invention has a preferred weight average molecular weight of from about 500 to about 500,000 and more, and comprises a chemical structure B as follows:

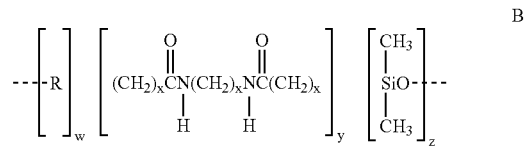

where R is, as discussed below, an oxyalkylene group such as —OEt-, etc. and w, x, y, and z are appropriate to meet the molecular weight. The variable x, which may be the same or different, is preferably 1-40, while w, and y are preferably 1-1000, preferably 1-100 including 10, 20, 30, 40, etc. Preferably z is 0-1000, more preferably 1-1000, even more preferably 1-200, even more highly preferably 1-100 including 10, 20, 30, 40, etc., and the ratio y/(w+z) optionally varies from 0.01 to 100, more preferably 1-10. Preferably the ratio z/w varies from 0.001-1000, including 0.01-100, 1-10, 2-8, etc. Where the ratio z/w=0, no z unit is present, and w is nonzero. Preferably, w is never zero.

Another preferred self-emulsifying copolymer according to the invention has a preferred weight average molecular weight of from about 500 to about 500,000 and more, and comprises a chemical structure C as follows:

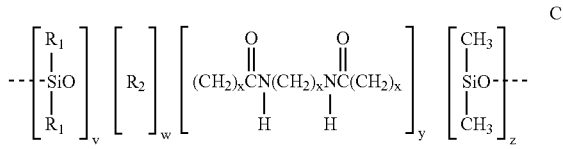

where at least one $R_1$, and $R_2$, is an oxyalkylene group such as —OEt-, etc., any $R_1$ that is not oxyalkylene, if any, is H or a C1-C12 alkyl group, preferably methyl or ethyl, The variable x, which may be the same or different, is preferably 1-40. Preferably z is 0-1000, more preferably 1-1000, even more preferably 1-200, even more highly preferably 1-100 including 10, 20, 30, 40, etc. Preferably y is 1-1000, more preferably 1-200, even more preferably 1-100 including 10, 20, 30, 40, etc. Preferably w is 0-1000, more preferably 1-1000, even more preferably 1-200, even more highly preferably 1-100 including 10, 20, 30, 40, etc. Preferably v is 0-1000, more preferably 1-1000, even more preferably 1-200, even more highly preferably 1-100 including 10, 20, 30, 40, etc. However, v and w cannot both be 0. Preferably the ratio y/(v+w+z) optionally varies from 0.01 to 100, more preferably 1-10, including all values between all ranges but where y is not zero and (v+w) is not zero. Preferably the ratio z/(w+v) varies from 0.001-1000, including 0.01-100, 1-10, 2-8, etc, including all values between all ranges, and when equal to zero means z=0 and (v+w) does not equal zero. The ratio v/w may vary from 0.01-100. In addition, either one of v or w may be zero, but (v+w) is never zero.

These self-emulsifying copolymers may be made by art accepted means, for example by polymerizing the necessary monomers, grafting existing blocks, etc. Such techniques are well known to, and within the skill of, the ordinary artisan in view of this disclosure. The disclosures in U.S. Pat. No. 5,412,004, U.S. Pat. No. 5,874,069, U.S. Pat. No. 5,919,441, U.S. Pat. No. 6,051,216, and U.S. Pat. No. 5,981,680 are all incorporated herein by reference. The terminal groups of the invention copolymers are not limited, and include those typical of, e.g., both polyamides and polysiloxanes. For example, Me3Si(O)— groups may be used. In addition, the invention copolymers can include polymerized monomer units other than those depicted above and described below, although in a preferred embodiment those depicted in formulae A-C above and those described below make up a totality of the copolymer but for the terminal groups.

Preferred oxyalkylene groups (alkylene oxide groups) according to the invention (OR) are —O-ethyl-, —O-propyl-, —O-isopropyl-, etc. Preferably, the oxyalkylene groups are polyoxyalkylene groups of the formulae

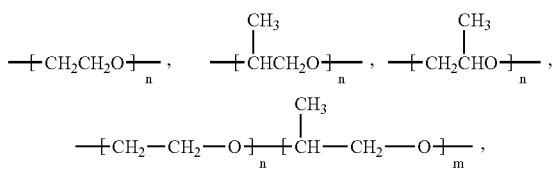

including mixtures of ethylene oxide, propylene oxide, isopropylene oxide, etc. in the same alkylene oxide chain. In these formulae n and m are not limited and may be 1-1000 and more, preferably 1-200, more preferably 2-60, 2-50, 4-35, etc. As is known to those of ordinary skill, the terminus of such groups typically is H. Other useful alkylene oxides are described in U.S. Pat. No. 5,412,004, incorporated herein by reference. These preferred oxyalkylene groups, described in this paragraph, are sometimes referred to herein as (poly)oxyalkylene groups.

Another preferred polymer that, when prepared or synthesized to include at least one alkylene-oxide containing group R2 and/or R1, is a polymer preferably having a weight-average molecular weight ranging from 500 to 500 000 or more, comprising at least one moiety comprising:

at least one polyorganosiloxane group, preferably having from 1 to 1 000 organosiloxane units in the chain of the moiety or in the form of a graft, and at least two groups, which may be the same or different, capable of establishing hydrogen interactions, chosen from ester, amide, sulphonamide, carbamate, thiocarbamate, urea, urethane, thiourea, oxamido, guanamido and biguanidino groups, and combinations thereof, the polymer preferably being solid at 25° C. and soluble in the fatty phase at a temperature of from 25 to 250° C. The polymer in general is preferably solid at room temperature (25° C.) and atmospheric pressure (760 mm Hg) and soluble in an oil and/or liquid fatty phase at a temperature of from 25 to 250° C. Such materials are prepared by incorporating alkylene oxide groups R1 and/or SiO2(R1)(R1) described above within the backbone of the polymer. These polymers may be made as generally described above by synthesizing the polymer with one or more alkylene oxide (OR)-containing groups R2 and/or SiO2(R1)(R1) in the backbone thereof, where R1 and R2 are as defined above. In such modified copolymers, at least one alkylene oxide-containing group is present.

Useful polymers that similarly may be synthesized or prepared by incorporating one or more alkylene oxide (OR)— containing groups R2 and/or SiO2(R1)(R1) in the backbone thereof will now be described. In these polymers and those described above the alkylene oxide (OR)— containing groups R2 and/or SiO2(R1)(R1) are present preferably in an amount that provides the property of self-emulsification. In a preferred embodiment the alkylene oxide (OR)— containing groups R2 and SiO2(R1)(R1) make up from 0.05-75 and more mol percent of the monomer units making up the polymer, including 0.1, 0.3, 0.5, 0.8, 1, 2, 3, 4, 5, 6, 7, 8, 9, 10, 12, 15, 18, 20, 22, 25, 28, 30, 35, 40, etc. mol %.

Accordingly, useful polymers that may be synthesized or prepared by incorporating alkylene oxide (OR)— containing groups R2 and/or SiO2(R1)(R1) as described above in the backbone thereof include polymers comprising at least one moiety corresponding to the formula:

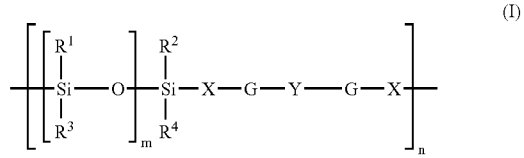

in which:

1) $R^1$, $R^1R^3$ and $R^4$, which may be identical or different, represent a group chosen from:

linear, branched or cyclic, saturated or unsaturated, $C_1$ to $C_{40}$ hydrocarbon-based groups, possibly containing in their chain one or more oxygen, sulphur and/or nitrogen atoms, and possibly being partially or totally substituted with fluorine atoms, $C_6$ to $C_{10}$ aryl groups, optionally substituted with one or more $C_1$ to $C_4$ alkyl groups, polyorganosiloxane chains possibly containing one or more oxygen, sulphur and/or nitrogen atoms;

2) the groups X, which may be identical or different, represent a linear or branched $C_1$ to $C_{30}$ alkylenediyl group, possibly containing in its chain one or more oxygen and/or nitrogen atoms;

3) Y is a saturated or unsaturated, $C_1$ to $C_{50}$ linear or branched divalent alkylene, arylene, cycloalkylene, alkylarylene or arylalkylene group, possibly comprising one or more oxygen, sulphur and/or nitrogen atoms, and/or bearing as substituent one of the following atoms or groups of atoms:

fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or 4) Y represents a group corresponding to the formula:

in which

T represents a linear or branched, saturated or unsaturated, $C_3$ to $C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and $R^5$ represents a linear or branched $C_1$ to $C_{50}$ alkyl group or a polyorganosiloxane chain, possibly comprising one or more ester, amide, urethane, thiocarbamate, urea, urethane, thiourea and/or sulphonamide groups, which may be linked to another chain of the polymer;

5) the groups G, which may be identical or different, represent divalent groups chosen from:

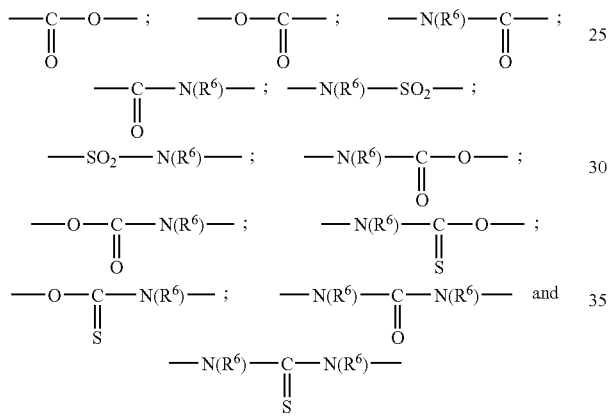

in which $R^6$ represents a hydrogen atom or a linear or branched $C_1$ to $C_{20}$ alkyl group, on condition that at least 50% of the groups $R^6$ of the polymer represents a hydrogen atom and that at least two of the groups G of the polymer are a group other than:

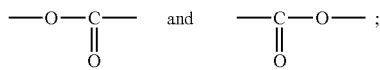

6) n is an integer ranging from 2 to 500 and preferably from 2 to 200, and m is an integer ranging from 1 to 1 000, preferably from 1 to 700 and better still from 6 to 200.

According to the invention, 80% of the groups $R^1$, $R^2$, $R^3$ and $R^4$ of the polymer are preferably chosen from methyl, ethyl, phenyl and 3,3,3-trifluoropropyl groups.

According to the invention, Y can represent various divalent groups, furthermore optionally comprising one or two free valencies to establish bonds with other moieties of the polymer or copolymer. Preferably, Y represents a group chosen from:

a) linear $C_1$ to $C_{20}$ and preferably $C_1$ to $C_{10}$-alkylene groups, b) $C_{30}$ to $C_{56}$ branched alkylene groups possibly comprising rings and unconjugated unsaturations, c) $C_5$-$C_6$ cycloalkylene groups, d) phenylene groups optionally substituted with one or more $C_1$ to $C_{40}$ alkyl groups, e) $C_1$ to $C_{20}$ alkylene groups comprising from 1 to 5 amide groups, f) $C_1$ to $C_{20}$ alkylene groups comprising one or more substituents chosen from hydroxyl, $C_3$ to $C_8$ cycloalkane, $C_1$ to $C_3$ hydroxyalkyl and $C_1$ to $C_6$ alkylamine groups, g) polyorganosiloxane chains of formula:

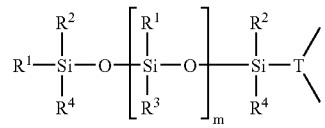

in which $R^1$, $R^2$, $R^3$, $R^4$, T and m are as defined above, and h) polyorganosiloxane chains of formula:

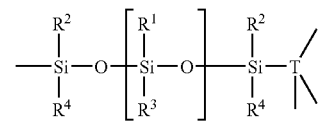

in which $R^1$, $R^2$, $R^3$, $R^4$, T and m are as defined above.

The polyorganosiloxanes of the second family may be polymers comprising at least one moiety corresponding to formula (II):

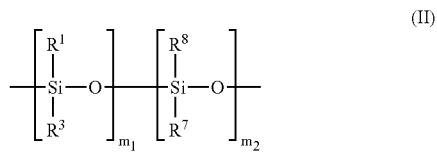

(II)

in which $R^1$ and $R^3$, which may be identical or different, are as defined above for formula (I), $R^7$ represents a group as defined above for $R^1$ and $R^3$, or represents a group of formula —X-G-$R^9$ in which X and G are as defined above for formula (I) and $R^9$ represents a hydrogen atom or a linear, branched or cyclic, saturated or unsaturated, $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups, $R^8$ represents a group of formula —X-G-$R^9$ in which X, G and $R^9$ are as defined above, $m_1$ is an integer ranging from 1 to 998, and $m_2$ is an integer ranging from 2 to 500.

According to the invention, the polymer used as structuring agent may be a homopolymer, that is to say a polymer comprising several identical moieties, in particular moieties of formula (I) or of formula (II).

According to the invention, it is also possible to use as a modifiable copolymer to modify one comprising several different moieties of formula (I), that is to say a polymer in which at least one of the groups $R^1$, $R^2$, $R^3$, $R^4$, X, G, Y, m and n is different in one of the moieties. The copolymer may also be formed from several moieties of formula (II), in which at least one of the groups $R^1$, $R^3$, $R^7$, $R^8$, $m_1$ and $m_2$ is different in at least one of the moieties.

It is also possible to use a copolymer comprising at least one moiety of formula (I) and at least one moiety of formula (II), the moieties of formula (I) and the moieties of formula (II) possibly being identical to or different from each other.

According to one variant of the invention, it is also possible to use a copolymer furthermore comprising at least one hydrocarbon-based moiety comprising two groups capable of establishing hydrogen interactions, chosen from ester, amide, sulphonamide, carbamate, thiocarbamate, urea, urethane, thiourea oxamido, guanamido and biguanidino groups, and combinations thereof.

These copolymers may be block copolymers or grafted copolymers.

Groups capable of establishing hydrogen interactions include amide groups of formulae —C(O)NH— and —HN—C(O)—.

In this case, the copolymer may be a polymer comprising at least one moiety of formula (III) or (IV):

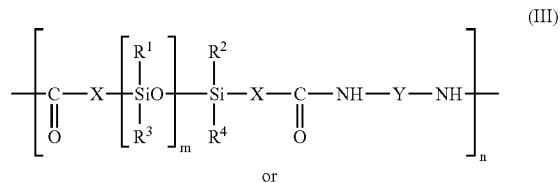
(III)

or

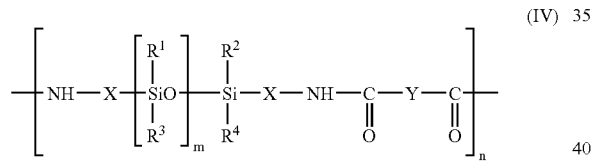
(IV)

in which $R^1$, $R^2$, $R^3$, $R^4$, X, Y, m and n are as defined above. Here, and in all formulae herein where R is bonded to Si, any or all of such R groups may be (poly) oxyalkylene $(RO)_n$.

Such a moiety may be obtained:
either by a condensation reaction between a silicone containing α,ω(co-carboxylic acid ends and one or more diamines, according to the following reaction scheme:

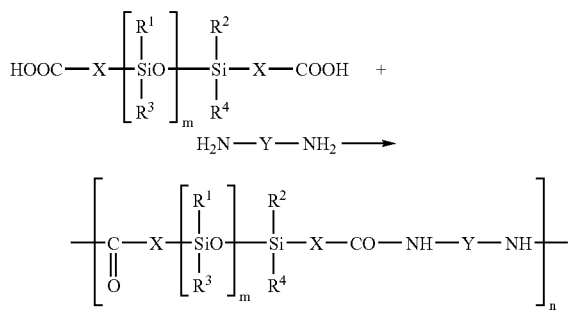

or by reaction of two molecules of α-unsaturated carboxylic acid with a diamine according to the following reaction scheme:

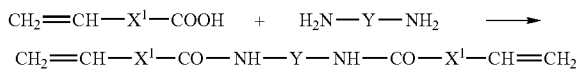

followed by the addition of a siloxane to the ethylenic unsaturations, according to the following scheme:

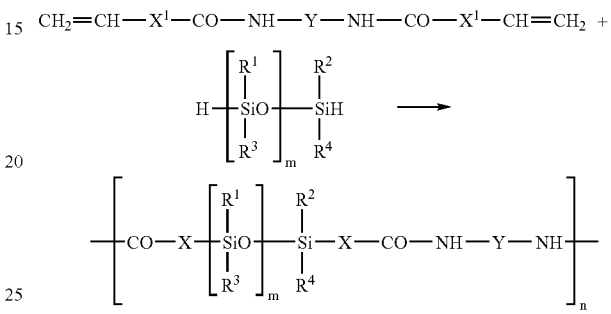

in which $X^1$—$(CH_2)_2$-corresponds to X defined above and Y, $R^1$, $R^2$, $R^3$, $R^4$ and m are as defined above;

or by reaction of a silicone containing αω-$NH_2$ ends and a diacid of formula HOOC—Y—COOH according to the following reaction scheme:

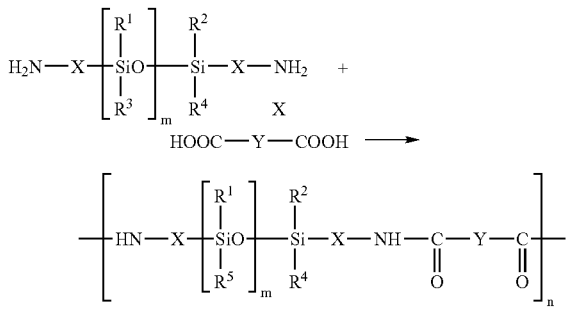

In these polyamides of formula (III) or (IV), m is preferably in the range from 1 to 700, more preferably from 15 to 500 and better still from 15 to 45, and n is in particular in the range from 1 to 500, preferably from 1 to 100 and better still from 4 to 25, X is preferably a linear or branched alkylene chain containing from 1 to 30 carbon atoms and in particular 3 to 10 carbon atoms, and Y is preferably an alkylene chain that is linear or branched or that possibly comprises rings and/or unsaturations, containing from 1 to 40 carbon atoms, in particular from 1 to 20 carbon atoms and better still from 2 to 6 carbon atoms, in particular 6 carbon atoms.

In formulae (III) and (IV), the alkylene group representing X or Y can optionally contain in its alkylene portion at least one of the following elements:

1°) 1 to 5 amide, urea or carbamate groups,
2°) a $C_5$ or $C_6$ cycloalkyl group, and 3°) a phenylene group optionally substituted with 1 to 3 identical or different $C_1$ to $C_3$ alkyl groups.

In formulae (III) and (IV), the alkylene groups may also be substituted with at least one element chosen from the group consisting of:

a hydroxyl group, a $C_3$ to $C_8$ cycloalkyl group, one to three $C_1$ to $C_{40}$ alkyl groups, a phenyl group optionally substituted with one to three $C_1$ to $C_3$ alkyl groups, a $C_1$ to $C_3$ hydroxyalkyl group, and a $C_1$ to $C_6$ aminoalkyl group.

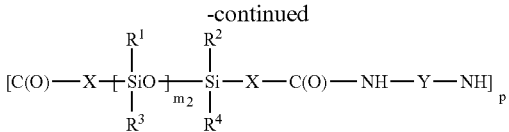

in which X, Y, n and $R^1$ to $R^4$ have the meanings given above, $m_1$ and $m_2$, which are different, are chosen in the range from 1 to 1 000, and p is an integer ranging from 2 to 300.

In this formula, the moieties may be structured to form either a block copolymer, or a random copolymer or an alternating copolymer. In this copolymer, the moieties may be not only of different lengths, but also of different chemical structures, for example containing different groups Y. In this case, the copolymer may correspond to the formula:

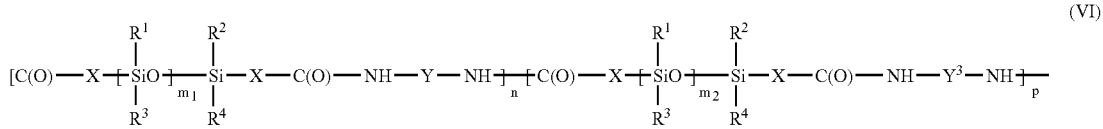

In these formulae (III) and (IV), Y may also represent:

in which $R^5$ represents a polyorganosiloxane chain and T represents a group of formula:

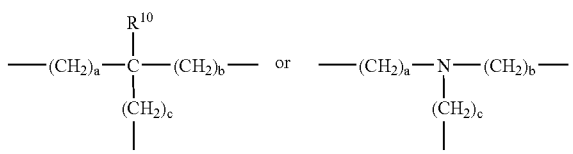

in which a, b and c are, independently, integers ranging from 1 to 10, and $R^{10}$ is a hydrogen atom or a group such as those defined for $R^1$, $R^2$, $R^3$ and $R^4$.

In formulae (III) and (IV), $R^1$, $R^2$, $R^3$ and $R^4$ preferably represent, independently, a linear or branched $C_1$ to $C_{40}$ alkyl group, preferably a $CH_3$, $C_2H_5$, n-$C_3H_7$ or isopropyl group, a polyorganosiloxane chain or a phenyl group optionally substituted with one to three methyl or ethyl groups.

As has been seen previously, the polymer may comprise identical or different moieties of formula (III) or (IV).

Thus, the polymer may be a polyamide containing several moieties of formula (III) or (IV) of different lengths, i.e. a polyamide corresponding to the formula:

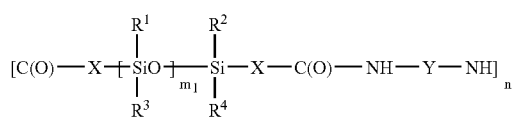

in which $R^1$ to $R^4$, X, Y, $m_1$, $m_2$, n and p have the meanings given above and $Y^1$ is different from Y but chosen from the groups defined for Y. As previously, the various moieties may be structured to form either a block copolymer, or a random copolymer or an alternating copolymer.

In this first embodiment of the invention, the structuring polymer may also consist of a grafted copolymer. Thus, the polyamide containing silicone units may be grafted and optionally crosslinked with silicone chains containing amide groups. Such polymers may be synthesized with trifunctional amines.

In this case, the copolymer may comprise at least one moiety of formula:

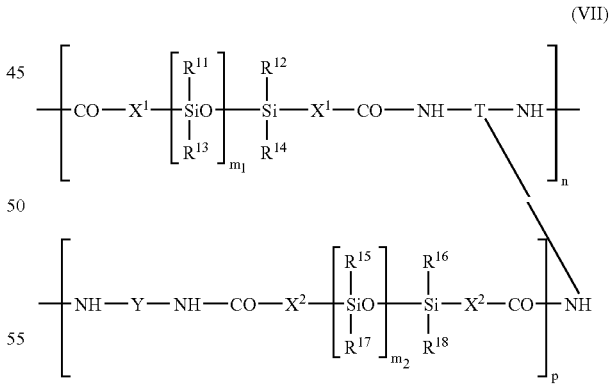

in which $X^1$ and $X^2$, which may be identical or different, have the meaning given for X in formula (I), n is as defined in formula (I), Y and T are as defined in formula (I), $R^{11}$ to $R^{18}$ are groups chosen from the same group as $R^1$ to $R^4$, $m_1$ and $m_2$ are numbers in the range from 1 to 1 000, and p is an integer ranging from 2 to 500.

In formula (VII), it is preferred that:

p is in the range from 1 to 25 and better still from 1 to 7, $R^{11}$ to $R^{18}$ are methyl groups, T corresponds to one of the following formulae:

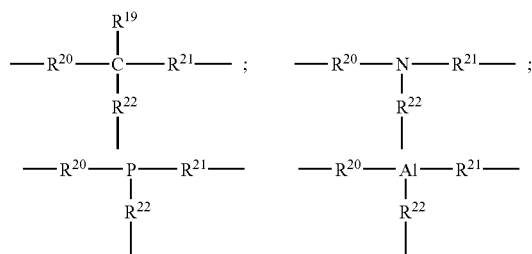

in which $R^{19}$ is a hydrogen atom or a group chosen from the groups defined for $R^1$ to $R^4$, and $R^{20}$, $R^{21}$ and $R^{22}$ are, independently, linear or branched alkylene groups, and more preferably corresponds to the formula:

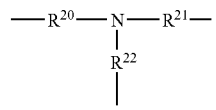

in particular with $R^{20}$, $R^{21}$ and $R^{22}$ representing —$CH_2$—$CH_2$—,
  $m_1$ and $m_2$ are in the range from 15 to 500 and better still from 15 to 45,
  $X^1$ and $X^2$ represent —$(CH_2)_{10}$—, and
  Y represents —$CH_2$—.

These polyamides containing a grafted silicone moiety of formula (VII) may be copolymerized with polyamide-silicones of formula (II) to form block copolymers, alternating copolymers or random copolymers. The weight percentage of grafted silicone moieties (VII) in the copolymer may range from 0.5% to 30% by weight.

According to the invention, the siloxane units may be in the main chain or backbone of the polymer, but they may also be present in grafted or pendent chains. In the main chain, the siloxane units may be in the form of segments as described above. In the pendent or grafted chains, the siloxane units may appear individually or in segments.

According to the invention, the preferred siloxane-based polyamides are:
  polyamides of formula (III) in which m is from 15 to 50;
  mixtures of two or more polyamides in which at least one polyamide has a value of m in the range from 15 to 50 and at least one polyamide has a value of m in the range from 30 to 50;
  polymers of formula (V) with $m_1$ chosen in the range from 15 to 50 and $m_2$ chosen in the range from 30 to 500 with the portion corresponding to m1 representing 1% to 99% by weight of the total weight of the polyamide and the corresponding portion $m_2$ representing 1% to 99% by weight of the total weight of the polyamide;
  mixtures of polyamide of formula (III) combining
    1) 80% to 99% by weight of a polyamide in which n is equal to 2 to 10 and in particular 3 to 6, and
    2) 1% to 20% of a polyamide in which n is in the range from 5 to 500 and in particular from 6 to 100;
  polyamides corresponding to formula (VI) in which at least one of the groups Y and $Y^1$ contains at least one hydroxyl substituent;
  polyamides of formula (III) synthesized with at least one portion of an activated diacid (diacid chloride, dianhydride or diester) instead of the diacid;
  polyamides of formula (III) in which X represents —$(CH_2)_3$— or —$(CH_2)_{10}$; and
  polyamides of formula (III) in which the polyamides end with a monofunctional chain chosen from the group consisting of monofunctional amines, monofunctional acids, monofunctional alcohols, including fatty acids, fatty alcohols and fatty amines, such as, for example, octylamine, octanol, stearic acid and stearyl alcohol.

According to the invention, the end groups of the polymer chain may end with:
  a $C_1$ to $C_{50}$ alkyl ester group by introducing a $C_1$ to $C_{50}$ monoalcohol during the synthesis,
  a $C_1$ to $C_{50}$ alkylamide group by taking as stopping group a monoacid if the silicone is αω-diaminated, or a monoamine if the silicone is an α,ω-dicarboxylic acid.

According to one embodiment variant of the invention, it is possible to use a copolymer of silicone polyamide and of hydrocarbon-based polyamide, i.e. a copolymer comprising moieties of formula (III) or (IV) and hydrocarbon-based polyamide moieties. In this case, the polyamide-silicone moieties may be arranged at the ends of the hydrocarbon-based polyamide.

Self-emulsifying copolymers may be produced by silylic amidation of polyamides based on fatty acid dimer. This approach involves the reaction of free acid sites existing on a polyamide as end sites, with organosiloxane-monoamines and/or organosiloxane-diamines (amidation reaction), or alternatively with oligosiloxane alcohols or oligosiloxane diols (esterification reaction). The esterification reaction requires the presence of acid catalysts, as is known in the art. It is desirable for the polyamide containing free acid sites, used for the amidation or esterification reaction, to have a relatively high number of acid end groups (for example polyamides with high acid numbers, for example from 15 to 20).

For the amidation of the free acid sites of the hydrocarbon-based polyamides, siloxane diamines with 1 to 300, more particularly 2 to 50 and better still 2, 6, 9.5, 12, 13.5, 23 or 31 siloxane groups, may be used for the reaction with hydrocarbon-based polyamides based on fatty acid dimers. Siloxane diamines containing 13.5 siloxane groups are preferred, and the best results are obtained with the siloxane diamine containing 13.5 siloxane groups and polyamides containing high numbers of carboxylic acid end groups.

The reactions may be carried out in xylene to extract the water produced from the solution by azeotropic distillation, or at higher temperatures (about 180 to 200° C.) without solvent. Typically, the efficacy of the amidation and the reaction rates decrease when the siloxane diamine is longer, that is to say when the number of siloxane groups is higher. Free amine sites may be blocked after the initial amidation reaction of the diaminosiloxanes by reacting them either with a siloxane acid, or with an organic acid such as benzoic acid.

For the esterification of the free acid sites on the polyamides, this may be performed in boiling xylene with about 1% by weight, relative to the total weight of the reagents, of para-toluenesulphonic acid as catalyst.

These reactions carried out on the carboxylic acid end groups of the polyamide lead to the incorporation of silicone moieties only at the ends of the polymer chain.

It is also possible to prepare a copolymer of polyamide-silicone, using a polyamide containing free amine groups, by amidation reaction with a siloxane containing an acid group.

It is also possible to prepare a self-emulsifying copolymer based on a copolymer between a hydrocarbon-based polyamide and a silicone polyamide, by transamidation of a polyamide having, for example, an ethylene-diamine constituent, with an oligosiloxane-α,ω-diamine, at high temperature (for example 200 to 300° C.), to carry out a transamidation such that the ethylenediamine component of the original polyamide is replaced with the oligosiloxane diamine.

The copolymer of hydrocarbon-based polyamide and of polyamide-silicone may also be a grafted copolymer comprising a hydrocarbon-based polyamide backbone with pendent oligosiloxane groups.

This may be obtained, for example:

- by hydrosilylation of unsaturated bonds in polyamides based on fatty acid dimers;
- by silylation of the amide groups of a polyamide; or
- by silylation of unsaturated polyamides by means of an oxidation, that is to say by oxidizing the unsaturated groups into alcohols or diols, to form hydroxyl groups that are reacted with siloxane carboxylic acids or siloxane alcohols. The olefinic sites of the unsaturated polyamides may also be epoxidized and the epoxy groups may then be reacted with siloxane amines or siloxane alcohols.

The polymers comprising at least two urethane and/or urea groups in the backbone in addition to the required (poly)oxyalkylene groups may be polymers comprising at least one moiety corresponding to the following formula:

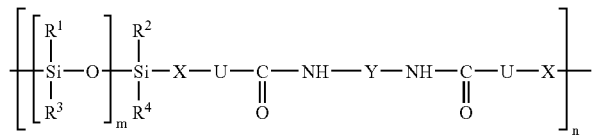

in which $R^1$, $R^2$, $R^3$, $R^4$, X, Y, m and n have the meanings given above for formula (I), and U represents —O— or —NH—, such that:

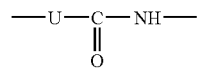

corresponds to a urethane or urea group. Here, any of $R^1$-$R^4$ may be (poly)oxyalkylene and in addition a (poly)oxyalkylene backbone block [OR] may be added thereto.

In this formula (VIII), Y may be a linear or branched $C_1$ to $C_{40}$ alkylene group, optionally substituted with a $C_1$ to $C_{15}$ alkyl group or a $C_5$ to $C_{10}$ aryl group. Preferably, a —(CH$_2$)$_6$— group is used.

Y may also represent a $C_5$ to $C_{12}$ cycloaliplatic or aromatic group that may be substituted with a $C_1$ to $C_{15}$ alkyl group or a $C_5$ to $C_{10}$ aryl group, for example a radical chosen from the methylene-4,4-biscyclohexyl radical, the radical derived from isophorone diisocyanate, 2,4- and 2,6-tolylenes, 1,5-naphthylene, p-phenylene and 4,4'-biphenylenemethane. Generally, it is preferred for Y to represent a linear or branched $C_1$ to $C_{40}$ alkylene radical or a $C_4$ to $C_{12}$ cycloalkylene radical.

Y may also represent a polyurethane or polyurea block corresponding to the condensation of several diisocyanate molecules with one or more molecules of coupling agents of the diol or diamine type. In this case, Y comprises several urethane or urea groups in the alkylene chain.

It may correspond to the formula:

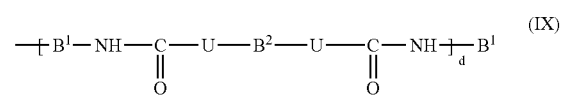

in which $B^1$ is a group chosen from the groups given above for Y, U is —O— or —NH— and $B^2$ is chosen from:

- linear or branched $C_1$ to $C_{40}$ alkylene groups, which can optionally bear an ionizable group such as a carboxylic acid or sulphonic acid group, or a neutralizable or quaternizable tertiary amine group,
- $C_5$ to $C_{12}$ cycloalkylene groups, optionally bearing alkyl substituents, for example one to three methyl or ethyl groups, or alkylene, for example the diol radical: cyclohexanedimethanol,
- phenylene groups that may optionally bear $C_1$ to $C_3$ alkyl substituents, and groups of formula:

in which T is a hydrocarbon-based trivalent radical possibly containing one or more hetero atoms such as oxygen, sulphur and nitrogen and $R^5$ is a polyorganosiloxane chain or a linear or branched $C_1$ to $C_{50}$ alkyl chain.

T can represent, for example:

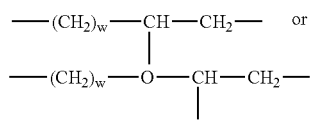

with w being an integer ranging from 1 to 10 and $R^5$ being a polyorganosiloxane chain.

When Y is a linear or branched $C_1$ to $C_{40}$ alkylene group, the —(CH$_2$)$_2$— and —(C$_1$H$_2$)$_6$— groups are preferred.

In the formula given above for Y, d may be an integer ranging from 0 to 5, preferably from 0 to 3 and more preferably equal to 1 or 2.

Preferably, $B^2$ is a linear or branched $C_1$ to $C_{40}$ alkylene group, in particular —(CH$_2$)$_2$— or —(CH$_2$)$_6$— or a group:

with $R^5$ being a polyorganosiloxane chain.

As previously, the self-emulsifying polymer may be formed from silicone urethane and/or silicone urea moieties of different length and/or constitution, and may be in the form of block or random copolymers.

According to the invention, the silicone may also comprise urethane and/or urea groups no longer in the backbone but as side branches.

In this case, the polymer may comprise at least one moiety of formula:

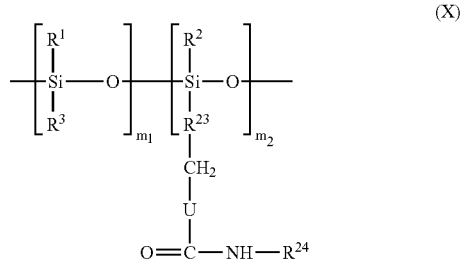

(X)

in which $R^1$, $R^2$, $R^3$, $m_1$ and $m_2$ have the meanings given above for formula (I), U represents O or NH, $R^{23}$ represents a $C_1$ to $C_{40}$ alkylene group, optionally comprising one or more hetero atoms chosen from O and N, or a phenylene group, and $R^{24}$ is chosen from linear, branched or cyclic, saturated or unsaturated $C_1$ to $C_{50}$ alkyl groups, and phenyl groups optionally substituted with one to three $C_1$ to $C_3$ alkyl groups.

The polymers comprising at least one moiety of formula (X) contain siloxane units and urea or urethane groups, and they may be used as structuring agents in the compositions of the invention.

The siloxane polymers may have a single urea or urethane group by branching or may have branches containing two urea or urethane groups, or alternatively they may contain a mixture of branches containing one urea or urethane group and branches containing two urea or urethane groups.

They may be obtained from branched polysiloxanes, comprising one or two amino groups by branching, by reacting these polysiloxanes with monoisocyanates.

As examples of starting polymers of this type containing amino and diamino branches, mention may be made of the polymers corresponding to the following formulae:

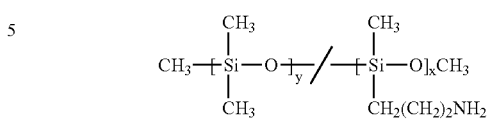

y = 57; x = 3

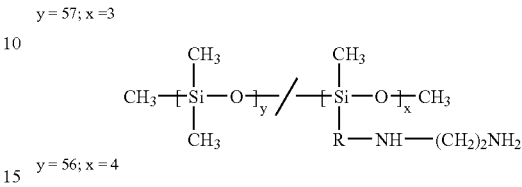

y = 56; x = 4

In these formulae, the symbol "/" indicates that the segments may be of different lengths and in a random order, and R represents a linear aliphatic group preferably containing 1 to 6 carbon atoms and better still 1 to 3 carbon atoms.

Such polymers containing branching may be formed by reacting a siloxane polymer, containing at least three amino groups per polymer molecule, with a compound containing only one monofunctional group (for example an acid, an isocyanate or an isothiocyanate) to react this monofunctional group with one of the amino groups and to form groups capable of establishing hydrogen interactions. The amino groups may be on side chains extending from the main chain of the siloxane polymer, such that the groups capable of establishing hydrogen interactions are formed on these side chains, or alternatively the amino groups may be at the ends of the main chain, such that the groups capable of hydrogen interaction will be end groups of the polymer.

As a procedure for forming a polymer containing siloxane units and groups capable of establishing hydrogen interactions, mention may be made of the reaction of a siloxane diamine and of a diisocyanate in a silicone solvent so as to provide a gel directly. The reaction may be performed in a silicone fluid, the resulting product being dissolved in the silicone fluid, at high temperature, the temperature of the system then being reduced to form the gel.

The polymers that are preferred for incorporation into the compositions according to the present invention are siloxane-urea copolymers that are linear and that contain urea groups as groups capable of establishing hydrogen interactions in the backbone of the polymer.

As an illustration of a polysiloxane ending with four urea groups, mention may be made of the polymer of formula:

(XI)
(Ph = Phenyl)

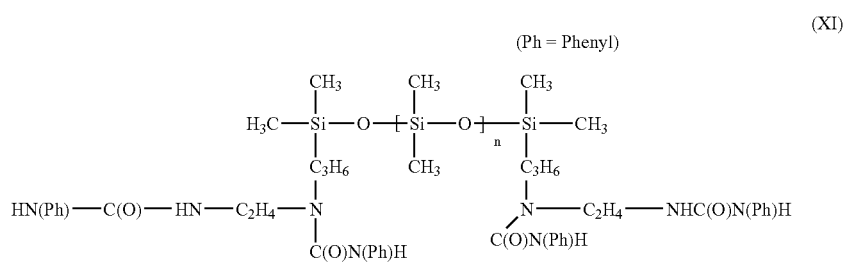

in which Ph is a phenyl group and n is a number from 0 to 300, in particular from 0 to 100, for example 50.

This polymer is obtained by reacting the following polysiloxane containing amino groups:

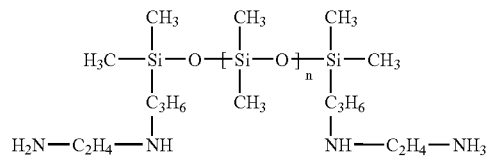

with phenyl isocyanate.

The polymers of formula (VIII) comprising urea or urethane groups in the chain of the silicone polymer may be obtained by reaction between a silicone containing α,ω-$NH_2$ or —OH end groups, of formula:

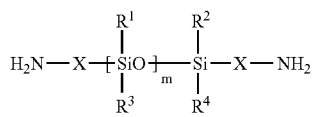

in which m, $R^1$, $R^2$, $R^3$, $R^4$ and X are as defined for formula (I) and a diisocyanate OCN—Y—NCO in which Y has the meaning given in formula (I); and optionally a diol or diamine coupling agent of formula $H_2N$—$B^2$—$NH_2$ or HO—$B^2$—OH, in which $B^2$ is as defined in formula (IX).

According to the stoichiometric proportions between the two reagents, diisocyanate and coupling agent, Y may have the formula (IX) with d equal to 0 or d equal to 1 to 5.

As in the case of the polyamide silicones of formula (II) or (III), it is possible to use in the invention polyurethane or polyurea silicones containing moieties of different length and structure, in particular moieties whose lengths differ by the number of silicone units. In this case, the copolymer may correspond, for example, to the formula:

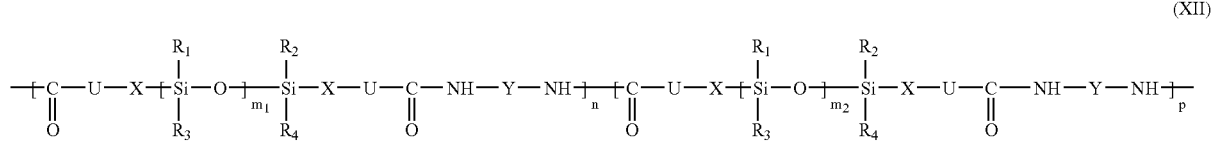

in which $R^1$, $R^2$, $R^3$, $R^4$, X, Y and U are as defined for formula (VIII) and $m_1$, $m_2$, n and p are as defined for formula (V).

Branched polyurethane or polyurea silicones may also be obtained using, instead of the diisocyanate OCN—Y—NCO, a triisocyanrate of formula:

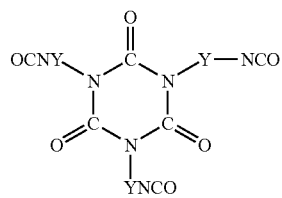

A polyurethane or polyurea silicone containing branches comprising an organosiloxane chain with groups capable of establishing hydrogen interactions is thus obtained. Such a polymer comprises, for example, a moiety corresponding to the formula:

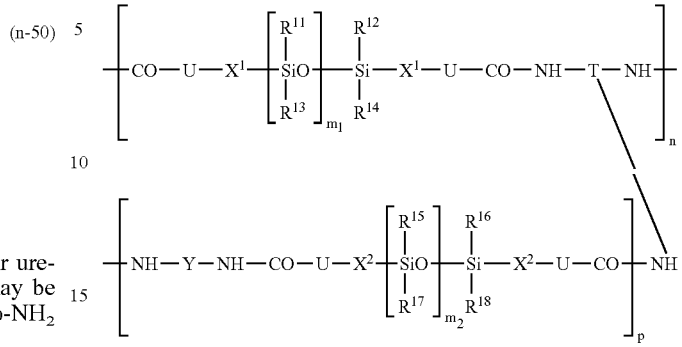

in which $X^1$ and $X^2$, which are identical or different, have the meaning given for X in formula (I), n is as defined in formula (I), Y and T are as defined in formula (I), $R^{11}$ to $R^{18}$ are groups chosen from the same group as $R^1$ to $R^4$, $m_1$ and $m_2$ are numbers in the range from 1 to 1 000, and p is an integer ranging from 2 to 500.

As in the case of the polyamides, this copolymer can also comprise polyurethane silicone moieties without branching.

In this second embodiment of the invention, the siloxane-based polyureas and polyurethanes that are preferred are:
  polymers of formula (VIII) in which m is from 15 to 50;
  mixtures of two or more polymers in which at least one polymer has a value of m in the range from 15 to 50 and at least one polymer has a value of m in the range from 30 to 50;
  polymers of formula (XII) with $m_1$ chosen in the range from 15 to 50 and $m_2$ chosen in the range from 30 to 500 with the portion corresponding to $m_1$ representing 1% to 99% by weight of the total weight of the polymer and the portion corresponding to $m_2$ representing 1% to 99% by weight of the total weight of the polymer;
  mixtures of polymer of formula (VIII) combining
  1) 80% to 99% by weight of a polymer in which n is equal to 2 to 10 and in particular 3 to 6, and
  2) 1% to 20% of a polymer in which n is in the range from 5 to 500 and in particular from 6 to 100,
  copolymers comprising two moieties of formula (VIII) in which at least one of the groups Y contains at least one hydroxyl substituent;
  polymers of formula (VIII) synthesized with at least one portion of an activated diacid (diacid chloride, dianhydride or diester) instead of the diacid;
  polymers of formula (VIII) in which X represents —$(CH_2)_3$— or —$(CH_2)_{10}$—; and
  polymers of formula (VIII) in which the polymers end with a multifunctional chain chosen from the group consisting of monofunctional amines, monofunctional acids, monofunctional alcohols, including fatty acids, fatty alcohols and fatty amines, such as, for example, octylamine, octanol, stearic acid and stearyl alcohol.

As in the case of the polyamides, copolymers of polyurethane or polyurea silicone and of hydrocarbon-based polyurethane or polyurea may be used in the invention by performing the reaction for synthesizing the polymer in the presence of an α,ω-difunctional block of non-silicone nature, for example a polyester, a polyether or a polyolefin.

As has been seen previously, the structuring polymer of the invention may contain siloxane moieties in the main chain of the polymer and groups capable of establishing hydrogen interactions, either in the main chain of the polymer or at the ends thereof, or on side chains or branches of the main chain. This may correspond to the following five arrangements:

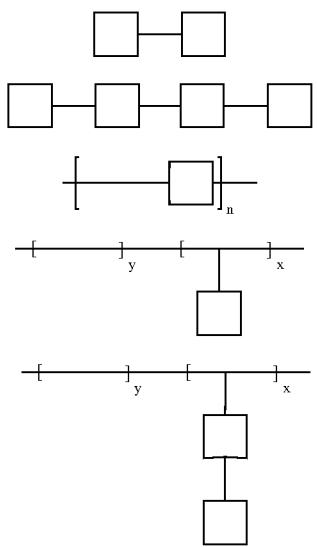

in which the continuous line is the main chain of the siloxane polymer and the squares represent the groups capable of establishing hydrogen interactions.

In case (1), the groups capable of establishing hydrogen interactions are arranged at the ends of the main chain.

In case (2), two groups capable of establishing hydrogen interactions are arranged at each of the ends of the main chain.

In case (3), the groups capable of establishing hydrogen interactions are arranged within the main chain in repeating moieties.

In cases (4) and (5), these are copolymers in which the groups capable of establishing hydrogen interactions are arranged on branches of the main chain of a first series of moieties that are copolymerized with moieties not comprising groups capable of establishing hydrogen interactions. The values n, x and y are such that the polymer has the desired properties in terms of an agent for gelling fatty phases based on silicone oil.

As further examples of polymers that may be used, mention may be made of the silicone polyamides obtained in accordance with Examples 1 and 2 of document U.S. Pat. No. 5,981,680.

The invention composition preferably comprises at least one invention self-emulsifying copolymer and a medium, preferably a physiologically acceptable medium. Preferably the medium comprises water. The invention composition may be in any form, such as that of a tube or stick, a paste, a cream, an emulsion, a gel, etc. In a preferred embodiment the invention composition is in the general form of a rigidified or solid gel that is reversible thermally and/or upon the application of shear. Such structured, e.g., gelled and/or rigidified, compositions are useful in cosmetic and/or dermatological products; this is especially the case in solid compositions such as deodorants, lip balms, lipsticks, concealer products, eye shadows and cast foundations.

The invention applies not only to make-up products for the lips, such as lipsticks, lip glosses and lip pencils, but also to care and/or treatment products for the skin, including the scalp, and for the lips, such as antisun care products for the human face, the body or the lips, such as in stick form, make-up removing products for the skin of the face and body, make-up products for the skin, both of the human face and body, such as foundations optionally cast in stick or dish form, concealer products, blushers, eyeshadows, face powders, transfer tattoos, body hygiene products (i.e., products which do not relate to the care, make-up, or treatment of keratin materials) such as deodorant, e.g., in stick form, shampoos, conditioners and make-up products for the eyes such as eyeliners, eye pencils and mascaras, e.g., in cake form, as well as make-up and care products for superficial body growths, for instance keratinous fibers such as the hair, the eyelashes, and the eyebrows or nails. Overall, it is of course preferred that the invention composition as a whole constitute a physiologically acceptable medium, in view of its usefulness in the cosmetic area.

The composition of the invention can also be in the form of a paste, a solid or a more or less viscous cream. It can be a single or multiple emulsion, such as an oil-in-water or water-in-oil emulsion or an oil-in-water-in-oil emulsion, or a water-in-oil-in-water emulsion, or a rigid or soft gel containing an oily continuous phase. For example, the liquid fatty phase can be the continuous phase of the composition. In one embodiment, which is highly preferred herein, the composition is anhydrous. In another embodiment, the composition is in a form cast as a stick or in a dish, for example solid, and further example, in the form of an oily rigid gel, such as an anhydrous gel, e.g., an anhydrous stick. In a further embodiment, the composition is in the form of an opaque or translucent rigid gel (depending on the presence or absence of pigments), and in a specific example, the liquid fatty phase forms the continuous-phase. In one embodiment, the composition is chosen from molded and poured sticks.

In the composition according to the present invention, the self-emulsifying copolymer preferably represents 0.1 to 99% by weight, more likely 0.5 to 80% by weight, more preferably 2 to 60% by weight, even more preferably 5 to 40% by weight, of the total weight of the composition. More or less may be used if desired, and these ranges include all values and subranges therebetween as if specifically written out.

The composition of the invention can also comprise any additive or ingredient used in the field under consideration, chosen for example and without limitation from dispersants such as poly(2-hydroxystearic acid), antioxidants, essential oils, preserving agents, fragrances, waxes, liposoluble polymers that are dispersible in the medium, fillers, neutralizing agents, cosmetic and dermatological active agents such as, for example, emollients, moisturizers, vitamins, essential fatty acids, sunscreens, colorants and mixtures thereof. These additives may be present in the composition in a proportion of from 0% to 20% (such as from 0.01% to 20%)

relative to the total weight of the composition and further such as from 0.01% to 10% (if present).

Needless to say, a person skilled in the art will take care to select the optional additional additives and/or the amount thereof such that the advantageous properties of the composition according to the invention are not, or are not substantially, adversely affected by the envisaged addition.

In this application, where a component of the invention is noted, whether in the specification or claims, more than one of such components may be present therein. That is, mixtures of invention components may be present in invention compositions. The term "and/or" means either one alone or both together. The expression "at least one" means one or more and thus includes individual components as well as mixtures/combinations. The expression "polymer" means a compound having at least two polymerized monomer units, preferably at least three such units more preferably at least ten such units. The term "about" means +/−10% unless otherwise specified. Whenever a numerical range or limit is expressed the endpoints are included therein, as is the norm. Also, all values and subranges within the stated range or limit are included as if specifically written out.

The invention claimed is:

1. A composition comprising a physiologically acceptable medium and a copolymer comprising the chemical formula:

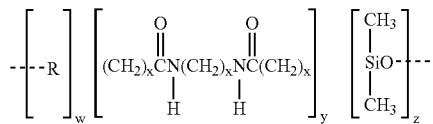

where R is an oxyalkylene group selected from the group consisting of oxyethylene, oxypropylene, oxyisopropylene, and mixtures thereof, x is 1-40, each of y and z is 1-200, and w is 2-200, wherein the copolymer has emulsifying activity and the ratio of z/w is from 0.001 to 1000.

2. The composition according to claim 1, wherein the oxyalkylene group is selected from the group consisting of

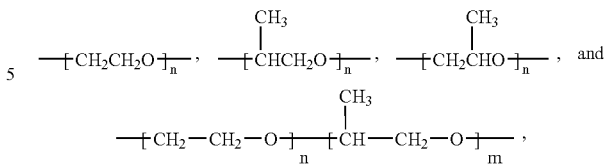

where n and m are each independently 1-100.

3. The composition of claim 1, further comprising water.

4. The composition of claim 3, wherein said composition is in the form of an emulsion.

5. The composition of claim 1, wherein said composition is in the form of an emulsion.

6. The composition according to claim 1, wherein w is from 2-100.

7. The composition according to claim 6, wherein said composition is in the form of an emulsion.

8. The composition according to claim 1, wherein w is from 2-40.

9. The composition according to claim 8, wherein said composition is in the form of an emulsion.

10. The composition according to claim 1, wherein w is from 10-100.

11. The composition according to claim 10, wherein said composition is in the form of an emulsion.

12. The composition according to claim 1, wherein w is from 10-40.

13. The composition according to claim 12, wherein said composition is in the form of an emulsion.

14. The composition according to claim 1, wherein w is from 10-30.

15. The composition of claim 14, wherein said composition is in the form of an emulsion.

16. The composition of claim 1, wherein the ratio of z/w is from 0.01 to 100.

17. The composition of claim 1, wherein the ratio of z/w is from 1 to 10.

18. The composition of claim 1, wherein the ratio of z/w is from 2 to 8.

* * * * *